US005783914A

United States Patent [19]
Hiramoto et al.

[11] Patent Number: 5,783,914
[45] Date of Patent: Jul. 21, 1998

[54] PARTICLE BEAM ACCELERATOR, AND A METHOD OF OPERATION

[75] Inventors: Kazuo Hiramoto, Hitachioota; Junichi Hirota, Hitachi; Masahiro Tadokoro, Hitachioota; Hiroaki Sakurabata, Hitachi, all of Japan

[73] Assignee: Hitachi, Ltd., Tokyo, Japan

[21] Appl. No.: 931,840

[22] Filed: Sep. 17, 1997

Related U.S. Application Data

[63] Continuation of Ser. No. 392,266, Feb. 22, 1995, abandoned.

[30] Foreign Application Priority Data

Mar. 17, 1994 [JP] Japan ................... 6-046760

[51] Int. Cl.$^6$ ................................. H05H 11/00
[52] U.S. Cl. .................. 315/504; 315/507; 250/492.3; 378/65
[58] Field of Search ...................... 315/504, 500, 315/507; 313/62; 250/492.3, 398; 378/64, 65

[56] References Cited

U.S. PATENT DOCUMENTS

| | | | |
|---|---|---|---|
| 4,870,287 | 9/1989 | Cole et al. | 250/492.3 |
| 5,285,166 | 2/1994 | Hiramoto et al. | 315/507 |
| 5,363,008 | 11/1994 | Hiramoto et al. | 315/500 |

FOREIGN PATENT DOCUMENTS

| | | | |
|---|---|---|---|
| 4-39899 | 2/1992 | Japan | H05H 7/00 |
| 4-197273 | 7/1992 | Japan | H05H 13/04 |
| 5-3100 | 1/1993 | Japan | H05H 13/04 |
| 5-198397 | 8/1993 | Japan | H05H 13/04 |
| 6-5397 | 1/1994 | Japan | H05H 13/04 |

OTHER PUBLICATIONS

Proceedings of the 7th Symposium on Accelerator Science and Technology, Dec. 12–14, 1989, pp. 48–50.
A.M. Koehler et al, "Range Modulators for Protons and Heavy Ions", Nuclear Instruments and Methods 131, 1975, pp. 437–440.

*Primary Examiner*—Sandra L. O'Shea
*Assistant Examiner*—Michael Day
*Attorney, Agent, or Firm*—Fay, Sharpe, Beall, Fagan, Minnich & McKee

[57] ABSTRACT

The present invention provides apparatus for acceleration of a charged particle beam which includes energy means for altering the energy of a circulating beam circulating in the apparatus and means for extracting output beams from the apparatus. Control means are arranged to be operable to alter the energy of the circulating beam using the energy means so as to be able to extract output beams of at least two energies from the apparatus using the means for extracting. Thus there is provided an accelerator, and an extraction method therefor, which is capable of extracting a small diameter beam having a varying energy level. This facilitates improved medical irradiation treatment using the beam.

24 Claims, 12 Drawing Sheets

Momentum P
Beam energy E

Intensity of deflecting magnetic field

Intensity of quadrupolar magnetic field

Intensity of hexapolar magnetic field

Ratios of intensities of magnetic fields

Acceleration frequency (orbiting frequency)

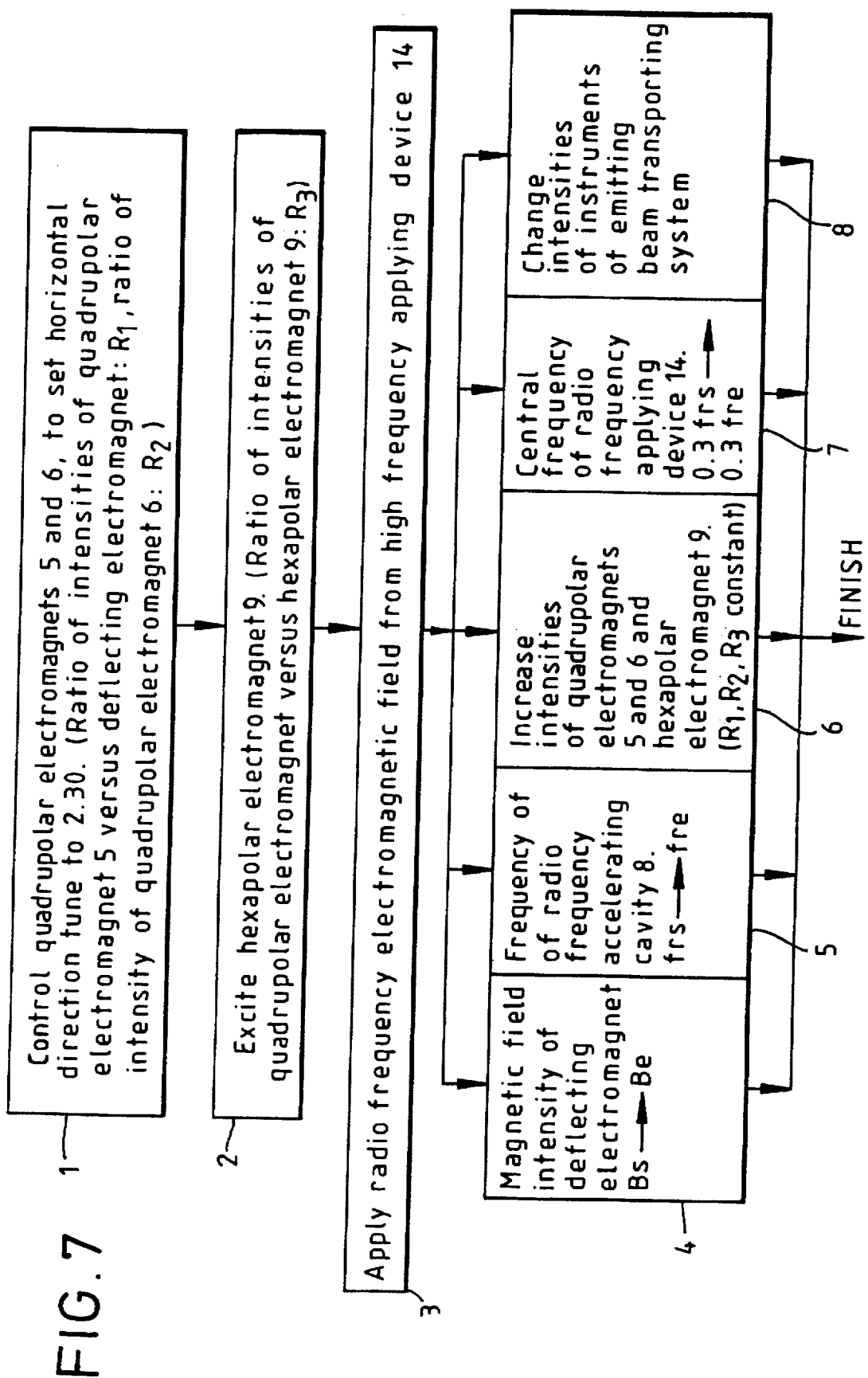

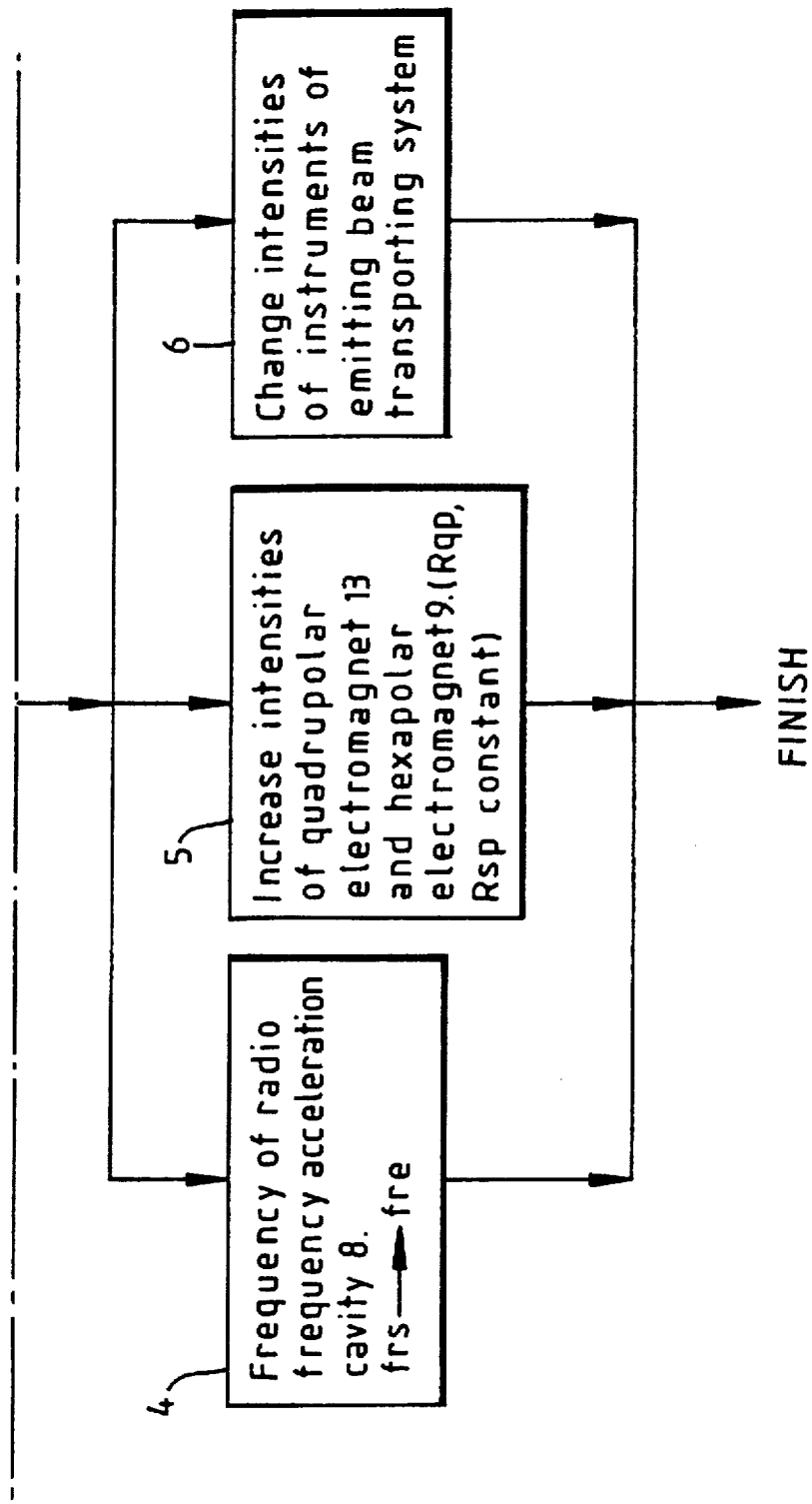

PARTICLE BEAM ACCELERATOR, AND A METHOD OF OPERATION

This is a continuation application of Ser. No. 08/392,266, filed Feb. 22, 1995, now abandoned.

BACKGROUND OF THE INVENTION

1. Field of the Invention

The present invention relates to an accelerator and method of operation therefor, and particularly to an accelerator which is suitable for use in medical irradiation treatment.

2. Description of the Prior Art

U.S. Pat. No. 5,285,166 discloses a charged particle accelerator which includes a bending magnet and a multipole magnet, with both magnets being for control of the orbit of the charged particles in the accelerator. A beam is extracted from the accelerator by adjusting the equilibrium orbit of the charged particles using either the bending magnet or the multipole magnet, thereby changing the tune of the charged particles. The aim of this method of extraction is to keep the gradient of the orbit of the extracted beam substantially constant.

Japanese Patent Application JP-A-198397/1993 discloses a beam accelerator which is illustrated in FIG. 2, and given reference numeral 101. In this accelerator, a beam is extracted by generating a resonance in a betatron oscillation of a charged particle beam orbiting in the accelerator 101, and the extracted beam is then transported to a medical treatment chamber 103 for use in an irradiation medical treatment.

A resonance phenomenon of a betatron oscillation is utilized in extracting a beam from this accelerator, and this is explained in more detail below.

The charged particles orbit in the accelerator while oscillating horizontally or vertically, and this is called the betatron oscillation. A frequency per one turn of an orbital path of the betatron oscillation is called a "tune", and the tune can be controlled by quadrupole electromagnets. When the tune is made near to a value of (integer+⅓), (integer+⅔), or (integer+½) by using quadrupole electromagnets 5 for converging and quadrupole electromagnets 6 for diverging the path of the charged particles respectively together with a hexapole electromagnet 9 for generating a resonance which is imposed on the orbital path, then an amplitude of the betatron oscillation of those of the orbiting charged particles which already have an amplitude of betatron oscillation at or exceeding a certain boundary rapidly increases. This phenomenon is called the resonance of the betatron oscillation. The boundary for generating the resonance is called a stability limit, the size of which varies according to magnetic field intensities of the quadrupole electromagnets and the multipole electromagnets.

The resonance when the tune is made near to (integer+½) is called a second order resonance, and the resonance when the tune is made near to (integer+⅔) is called a third order resonance. An explanation will now be given of an example in which the tune is made near to (integer+⅓). The smaller the deviation of the tune from (integer+⅓), and the stronger the magnetic field intensity of the hexapole electromagnet 9, the smaller the size of the stability limit of the resonance.

In one method of beam extraction, which may be used with the accelerator shown in FIG. 2, the tune is made near to (integer+⅓) to some degree while maintaining constant the intensity of the hexapole electromagnet 9, and resonance is generated in those charged particles having a large amplitude of betatron oscillation among the orbiting charged particles. Thereafter, the tune is made nearer to (integer+⅓), which narrows the stability limit, thereby also generating resonance also for charged particles having a smaller amplitude of oscillation. The beam energy is maintained constant in this procedure. Such a control of the tune is performed by controlling the magnetic field intensities of the quadrupole electromagnets 5 and 6 which are installed on the orbital path, as shown in FIG. 2.

A further method of beam extraction is disclosed in JP-A-198397/1993. This comprises a method of generating a resonance by increasing the amplitude of the betatron oscillation while maintaining constant not only the intensities of the bending electromagnets 2 and the hexapole electromagnet 9, but also the tune, that is, the magnetic field intensity of the quadrupole electromagnets.

In this beam extracting method the resonance is generated by increasing the amplitude of the betatron oscillation by applying a radio frequency electromagnetic field from a radio frequency applying device 14 in a direction orthogonal to the progressing direction of the beam, while at the same time maintaining constant the stability limit of the resonance by the constant tune. Furthermore in this extracting method the beam energy is also maintained at a constant level.

The extracted beam is transported to the medical treatment chamber 103 where it may be used to irradiate a body. When an ion beam enters an internal tissue of the body in the irradiation medical treatment energy is given off into the tissue. The amount of energy given off at a particular depth varies with the depth, as shown in FIG. 3. The depth at which maximum irradiation occurs is called Bragg's peak (reference numeral 300 in FIG. 3), and the position of Bragg's peak is determined by the beam energy. In an irradiation medical treatment the Bragg's peak for the beam is matched to the desired depth of irradiation of the affected part.

The position of Bragg's peak and the characteristic of the irradiation amount proximate to Bragg's peak are controlled by using a range controller 106, as shown in FIG. 4, while maintaining a constant beam energy for the beam extracted from the accelerator.

However, generally the position of an affected part is different for different patients, and therefore the desired depth of maximum irradiation (and hence desired beam energy) will be different. Additionally the size of the affected part may be such that radiation is required at a range of depths, which range exceeds a range proximate to Bragg's peak of the beam. In order to adjust this depth, or to provide radiation at a range of depths, it is necessary to change the range controller which necessitates interrupting the beam extraction process. In the case of a single patient this means that the treatment must be interrupted, and in the case of adjustment between patients this means that there is a considerable time delay between the treatment of different patients.

A range controller is described in Nuclear Instruments and Methods 131 (1975) pp. 437–440, wherein the beam is controlled by passing it through a heavy metal or a plastic glass range controller. In this case, it is necessary to change the shape or the size or the like of the range controller in accordance with the depth or the size of the affected part to be treated, and it is therefore necessary to use a number of different range controllers.

In a paper entitled "Beam Delivery System of HIMAC", by H Ogawa et al from the proceedings of the 7th Symposium on Accelerator Science and Technology (pages 48–50), aspects of the proposed design for the HIMAC (Heavy Iron Medical Accelerator in Chiba) are disclosed. The design includes the provision of a variety of transport lines to transport beams extracted from the accelerator to a number of different medical treatment rooms.

The above described technology has the following problems.

Firstly, it is difficult to change the beam energy whilst a beam is being extracted. Secondly, when the range controller is used for changing the beam energy the beam diameter may be enlarged and the beam characteristic may be deteriorated. Thirdly, in a medical device it is necessary to utilize range controllers each of which may need to be different for each patient and therefore, considerable time is required in selecting and/or positioning or the like of the range controller. Therefore, the waiting time until a patient receives the irradiation treatment may be considerable.

SUMMARY OF THE INVENTION

The present invention aims to provide an accelerator which mitigates some or all of the above problems.

Accordingly, in a first aspect the present invention provides a circulation chamber for circulation of a charged particle beam, and energy means for altering the energy of a circulating beam circulating in the circulation chamber, and extraction means for extracting output beams from the apparatus. Control means are arranged to be operable to alter the energy of the circulating beam using the energy means so as to be able to extract output beams of at least two energies from the apparatus using the extraction means whilst maintaining the circulating beam circulating in the apparatus.

Thus the energy of the beam (which may, for example, be being used for irradiation of a patient) can be changed without needing to shut down the acceleration apparatus, i.e. stop the circulating beam.

The duration of the output beams may be of any length and may be extremely short. Preferably the output beams are joined together so that in effect the output of the extraction means is a continuous beam having at least two energy levels at different times. In this case, the control means are arranged to be operable to extract the output beams sequentially using the extraction means so that the output beams are joined to form a continuous beam.

Preferably, the control means are arranged to be operable to alter the energy of the circulating beam using the energy means at the same time as extracting the output beams using the extraction means. Thus the energy level of the output beams may be varied without necessitating discontinuation of the extraction of the output beam.

Preferably, the extraction means include means for increasing an amplitude of a betatron oscillation of the circulating beam to exceed the stability limit of a resonance of the circulating beam, and the control means are operable to increase the amplitude at the same time as the energy means are operating.

Preferably, the means for increasing an amplitude of a betatron oscillation include means for applying a first electromagnetic field to the circulating beam in a direction transverse to the progressing direction (the direction of travel) of the circulating beam, and the control means are arranged to be operable to adjust the first electromagnetic field at the same time as the energy means are operating.

Preferably, the control means are arranged to be operable to alter the frequency of at least one component of the first electromagnetic field as the extraction means are operating.

Additionally or alternatively, preferably the energy means include means for applying a second electromagnetic field to the circulating beam in a direction along the progressing direction of the circulating beam, and the apparatus further includes bending (deflecting) and multipole magnets for producing first and second magnetic fields respectively to control the orbital path (the path of travel) of the circulating beam. The control means may be arranged to be operable to maintain the values of the first and second magnetic fields in a substantially constant ratio at the same time as the energy means are operating.

The apparatus may also include transportation means for transporting the output beams extracted (or emitted) from the circulation chamber, together with an electromagnet for controlling the output beams in the transportation means. The control means may be arranged to alter the magnetic field produced by the electromagnet in accordance with the energy of the output beams.

According to a second aspect, the present invention provides a method of operating a circular accelerator for a charged particle beam, the method including the steps of (i) maintaining a circulating beam circulating in a circulation chamber of the circular accelerator, (ii) changing the energy of the circulating beam during step (i), and (iii) extracting from the circulation chamber output beams of at least two energies during step (1).

Steps (ii) and (iii) may be carried out substantially simultaneously and/or the energy of at least one of the output beams may vary as it is extracted from the circulation chamber. Furthermore, the output beams may be joined to form a continuous beam and the energy of the continuous beam may vary as it is extracted from the circulation chamber.

Preferably, the step of extracting output beams includes the step of increasing an amplitude of a betatron oscillation of the circulating beam to exceed the stability limit of a resonance of the circulating beam. The stability limit may be maintained substantially constant as the amplitude of the betatron oscillation of the circulating beam is increased.

Preferably, the amplitude of the betatron oscillation is increased by applying a first electromagnetic field to the circulating beam in a direction transverse to the progressing direction of the circulating beam.

Preferably, the circular accelerator includes bending and multipole magnets for producing bending and multipole magnetic fields respectively, and both the bending and multipole magnetic fields remain substantially constant as the first electromagnetic field is varied.

Furthermore the first electromagnetic field may include a plurality of radio frequency components at different frequencies, and the frequency of at least one component of the first electromagnetic field may be altered as at least one of the output beams is extracted.

Preferably, the step of changing the energy of the circulating beam includes the steps of applying a second electromagnetic field to the circulating beam in a direction along the progressing direction of the circulating beam, and adjusting first and second magnetic fields produced by bending and multipole magnets respectively, the values of the first and second magnetic fields being maintained in a substantially constant ratio.

According to a further aspect, the present invention provides a method of operating an accelerator having a ring for a charged particle beam, the method including the steps of (i) changing the energy of the charged particle beam, and, at the same time, (ii) extracting the charged particle beam from the accelerator.

According to a further aspect, the present invention provides a method of irradiating a body with a charged particle beam, the method including the steps of varying the energy of the charged particle beam over a predetermined range during continuing irradiation of the body in order to adjust the depth in the body of maximum absorbtion of the charged particle beam. The predetermined range may be selected from within a range of 50 MeV to 800 MeV.

According to yet a further aspect, the present invention provides a method of varying the energy of an output charged particle beam over a predetermined range, the method including the step of adjusting the operation of the following elements of a circular charged particle beam acceleration apparatus: (i) accelerating means for altering the energy of a circulating beam circulating in the apparatus; (ii) extraction means for extracting the output charged particle beam from the apparatus; (iii) a bending magnet and a multipole magnet for controlling a path of the circulating beam; and (iv) a transport magnet for controlling the output charged particle beam.

According to a further aspect, the present invention provides a medical device having an accelerator for accelerating and extracting (i.e. emitting) a particle beam, and a transporting system for transporting to a medical treatment chamber an output beam which has been extracted from the accelerator, the medical treatment chamber being for performing an irradiation medical treatment using the output beam. A control device is included for controlling the accelerator and the transporting system.

The accelerator comprises accelerating means for accelerating the particle beam by providing an energy thereto, bending electromagnets for generating bending magnetic fields, a multipole electromagnet for generating a multipole magnetic field for specifying a stability limit of a resonance of the particle beam, and radio frequency applying means for increasing an amplitude of a betatron oscillation of the particle beam within the stability limit of the particle beam. The control device is adapted for controlling so as to maintain approximately constant both a ratio of intensities of the multipole magnetic field versus the bending magnetic fields, and a ratio of intensities of the bending magnetic fields versus a magnetic field in the transporting system.

According to a further aspect the present invention provides medical apparatus for irradiating a body with a charged particle beam, the apparatus including: (i) a charged particle beam accelerator having energy means for altering the energy of a circulating beam circulating in the apparatus, and means for extracting an output beam from the apparatus; and (ii) a controller including input means for input of a starting energy value and a finishing energy value for the output beam, the controller being adapted and arranged to control the charged particle beam accelerator to produce the required output beam.

According to a further aspect, the present invention provides apparatus for acceleration of a charged particle beam, the apparatus having a circulation chamber for circulation of a charged particle beam, energy means for altering the energy of a circulating beam circulating in the apparatus, means for extracting output beams from the apparatus; means for increasing an amplitude of a betatron oscillation of the circulating beam to exceed the stability limit of a resonance of the circulating beam which include means for applying a first electromagnetic field to the circulating beam in a direction transverse to the progressing direction of the circulating beam; wherein the energy means include means for applying a second electromagnetic field to the circulating beam in a direction along the progressing direction of the circulating beam, and the apparatus further includes bending and multipole magnets for producing first and second magnetic fields respectively to control the orbital path (path of travel) of the circulating beam, and a controller which is adapted to be operable to simultaneously control the energy of the circulating beam and the first electromagnetic field, whilst maintaining the values of the first and second magnetic fields in a substantially constant ratio at the same time as the energy means are operating.

According to a further aspect, the present invention provides an accelerator having electromagnets for orbiting a charged particle beam, and an extractor for extracting the beam, the accelerator comprising: accelerating means for accelerating the charged particle beam by providing an energy thereto; bending electromagnets for generating magnetic fields for bending the charged particle beam; a multipole electromagnet for generating a multipole magnetic field for specifying a stability limit of resonance of the charged particle beam; radio frequency applying means for increasing an amplitude of a betatron oscillation of the charged particle beam within the stability limit; and a control device for controlling so as to maintain substantially constant the intensities of the bending magnetic fields, and for controlling a frequency of an electric field or a magnetic field generated by the accelerating means and the radio frequency applying means to achieve a required change in energy of the charged particle beam.

Preferably, the control device controls a ratio of an intensity of the multipole magnetic field versus a momentum of the beam so as to maintain the ratio approximately constant.

Following is a general description of the operation of some embodiments of the present invention.

Firstly, an energy of a charged particle beam orbiting in an accelerator is varied during the extracting procedure. Control of the energy of the charged particle beam is performed by either of the following methods (1) and (2).

(1) The intensities of magnetic fields of the bending electromagnets and quadrupole electromagnets are varied by applying a radio frequency electric field in the progressing direction of the charged particle beam. During this step the ratio of intensities of the magnetic fields of the bending electromagnets to the intensity of the magnetic field of the quadrupole electromagnets is maintained approximately constant. If the charged particle is an ion, the frequency of the radio frequency electric field is also varied in accordance with the varying energy of the beam.

(2) The frequency of the radio frequency electric field is varied and is applied in the progressing direction of the charged particle beam while maintaining constant the intensity of the magnetic fields of the bending electromagnets.

The radio frequency electric field is generated by using, for instance, a radio frequency acceleration cavity.

Secondly, a multipole magnetic field for generating a resonance in the beam is generated by a multipole magnet such as a hexapole electromagnet or an octapolar electromagnet. When the energy of the orbiting beam is varied by method (1) in the extracting procedure, it is desirable to vary the intensity of the magnetic field of the multipole electromagnet such that the ratio of intensities of the magnetic field of the multipole electromagnetic versus the magnetic fields of the bending electromagnets is maintained substantially constant.

Thirdly, the amplitude of the betatron oscillation of the charged particle beam within the stability limit of the resonance of the beam is increased by applying the radio frequency electromagnetic field in a direction orthogonal to the progressing direction of the beam. In this case, the frequency spectrum of the radio frequency electromagnetic field is controlled in accordance with a change in the beam energy. The radio frequency electromagnetic field is generated by using, for instance, the radio frequency applying device.

Furthermore, the intensities of the instruments in the extracting beam transporting system which transports the beam to the medical treatment chamber may be varied in accordance with the change in the beam energy.

Next, an explanation will be given of the operation of an embodiment of the invention in the case where method (1) is used, and then in the case where method (2) is used.

According to the method (1), energy is provided to the beam using the radio frequency electric field, and, at the same time, the intensity of the magnetic fields of the bending electromagnets is varied. The radius of the curvature of the beam is determined by the beam energy and the intensity of the magnetic fields of the bending electromagnets. Therefore, it is possible to maintain substantially constant the radius of curvature of the beam in accordance with the change of the energy of the beam by varying the intensity of the magnetic fields of the bending electromagnetic fields. That is, the appropriate intensity of the magnetic fields of the bending electromagnets at the start and end of the extracting of a beam may be determined based on the beam energies at the start and end of the extracting.

When the intensity of the magnetic fields of the bending electromagnets is increased, the radius of curvature of the beam is decreased and the length of the orbital path of the beam in the accelerator is shortened. As a result, the period for one circulation of the beam decreases, and the phase of the applied radio frequency electric field at the time when the beam passes the accelerating cavity shifts to another phase so that the beam energy increases. In this way, the beam obtains the energy from the radio frequency electric field and the beam energy is increased.

At this stage in the operation of the accelerator, it is possible to make the tune of the beam substantially constant by controlling ratio of intensities of the magnetic fields of the quadrupole electromagnets versus the bending magnets so as to maintain that ratio substantially constant. It is also possible to maintain substantially constant the stability limit of the resonance by controlling so as to maintain substantially constant a ratio of intensities of the magnetic fields of the multipole electromagnets (used for exciting the resonance of the beam) versus the bending electromagnets, under an operating condition of constant tune.

Accordingly, it is possible to increase the beam energy while maintaining constant the stability limit of the resonance of the betatron oscillation of the beam. However, in a case where the change of the stability limit is small even when the intensities of the magnetic fields of the quadrupole electromagnets and the multipole electromagnet remain constant, the intensities of the magnetic fields of these electromagnets may be approximately constant.

Furthermore, when the charged particle is an ion, the beam energy may be increased by varying the frequency of the radio frequency electric field which is applied to the beam in accordance with the change in the energy of the beam, even if the orbiting frequency of the beam is changed in accordance with the change in energy of the beam.

In method (2), an energy is provided to the beam by changing the frequency of the radio frequency electric field which is applied to the beam, while maintaining substantially constant the intensity of the magnetic fields of the bending electromagnets. In this case, a phenomenon is utilized wherein, when the frequency of the radio frequency electric field is changed, the phase of the radio frequency electric field whereby the beam obtains the energy is also changed. Thus, there is an increase or a decrease in beam energy. However, the position of the beam is changed due to the change in the radius of curvature of the beam, since the intensity of the bending electromagnets is maintained constant.

Method (1) is applicable irrespective of the size of the change in the energy of the beam, whereas method (2) is more suitable for a case in which the change of energy is small. The reason for this is that, since the intensity of the magnetic fields of the bending electromagnets is maintained constant in method (2), the location of the central orbital path of the beam changes in accordance with the change in the energy of the beam, and therefore particles impinging on the vacuum duct increase in the case in which the change in the energy of the beam is large.

Furthermore, as in the third characteristic, it is possible to generate the resonance in the betatron oscillation by applying a radio frequency electromagnetic field in a direction orthogonal to the progressing direction of the beam, and thereby causing the beam exceed the stability limit by increasing the amplitude of the betatron oscillation of the beam (which has been stably orbiting within the stability limit of the resonance) while changing its energy, thereby extracting the beam.

Next, an explanation will be given of a method of increasing the amplitude of the betatron oscillation of particles within the stability limit of the resonance of the beam, using a radio frequency magnetic field or a radio frequency electric field in a direction orthogonal to the progressing direction of the beam.

The progressing direction of the beam in the accelerator is called the s direction, the horizontal direction the x direction, and the vertical direction the y direction. When using the radio frequency magnetic field, the field is applied in the vertical direction (y direction) when a plane (or face) of extracting the beam (extracting plane) is in a horizontal plane, whereas it is applied in the horizontal direction (x direction) when the extracting plane is in a vertical plane.

Although the change in the gradient of the orbital path of the beam at every turn of the accelerator due to the radio frequency magnetic field is small, the amplitude of the oscillation of the beam gradually increases by the accumulation thereof However, there is no special limitation with respect to the installing location of the device of applying the radio frequency magnetic field i.e. it may be located anywhere on the accelerator.

When increasing the amplitude of the betatron oscillation using the radio frequency magnetic field, it is desirable that the frequency of the radio frequency magnetic field is near to a frequency component in synchronism with the betatron oscillation. The frequency component in synchronism with the betatron oscillation is expressed as $(m+v)fr$ or $(m-v)fr$, where m is an integer, fr an orbiting frequency and $v$ the decimal portion of the tune.

Since the beam has a given energy distribution, particles having different energies are provided with different fr's. It is desirable to increase the amplitude of the betatron oscillation of all the particles having different energies. Therefore the radio frequency magnetic field may be provided with a plurality of frequency components, or with a continuous frequency band in which frequency components in synchronism with the betatron oscillation are contained in the frequency range. The time-varying change of the radio frequency magnetic field may be regular or irregular.

It is possible to utilize, for example, an electromagnet, a parallel lines type electrode, a plane electrode or a circular arc type electrode etc. as a device for applying the radio frequency magnetic field to the beam. It is possible to increase the amplitude of the betatron oscillation of the beam within the stability limit by powering these devices with a current signal which includes a frequency component which is near to a frequency component in synchronism with the betatron oscillation.

When the radio frequency electric field, the field may be applied in the s direction (which is the progressing direction of the beam), or in the horizontal direction (x direction) when the extracting plane of the beam is the horizontal plane, or in the vertical direction (y direction) when the extracting plane is the vertical plane. In this way, it is possible to increase the amplitude of the betatron oscillation of the beam within the stability limit, as in the case using the radio frequency magnetic field.

In the above ways, it is possible to increase the amplitude of the betatron oscillation of the beam within the stability limit using the radio frequency electric field or the radio frequency magnetic field in synchronism with the betatron oscillation. However, since the velocity of the beam changes by changing the beam energy in the extracting procedure in methods (1) and (2), the frequency in synchronism with the betatron oscillation also changes.

Accordingly, it is desirable to change the frequency of the radio frequency electromagnetic field in accordance with the change in the beam energy. When the radio frequency electromagnetic field is provided with a plurality of frequency components, it is preferable to change the respective ones. When it has a continuous frequency width, it is preferable to change all of the frequencies while the frequency width remains as it is. However, it is not necessary to change the frequency by using a radio frequency electromagnetic field having a wide frequency width including all the change of the frequencies in synchronism with the betatron oscillation.

As stated above, it is possible to extract a small diameter beam while changing the energy, since the beam can be extracted while maintaining constant the stability limit, even if the beam energy is continuously changed over time.

Further, it is possible to perform a beam irradiation medical treatment continuously over time, even if the affected parts have various depths or sizes, by changing the intensities of instruments of the extracting beam transporting system including the extractor, without using the conventionally employed range controller. Accordingly, it is possible to considerably shorten the waiting time until a patient receives irradiation medical treatment.

BRIEF INTRODUCTION TO THE DRAWINGS

Embodiments of the invention will now be described by way of non-limitative examples, with reference to the accompanying drawings, in which:

FIG. 7 is a flow chart showing an operational method for extracting a beam from the device of FIG. 1;

FIG. 9b is a view from above of the device of FIG. 9a;

FIGS. 12A and 12B are a flow chart showing an operational method for extracting a beam from the device of FIG. 10'

DETAILED DESCRIPTION OF EMBODIMENTS

Figure 1:
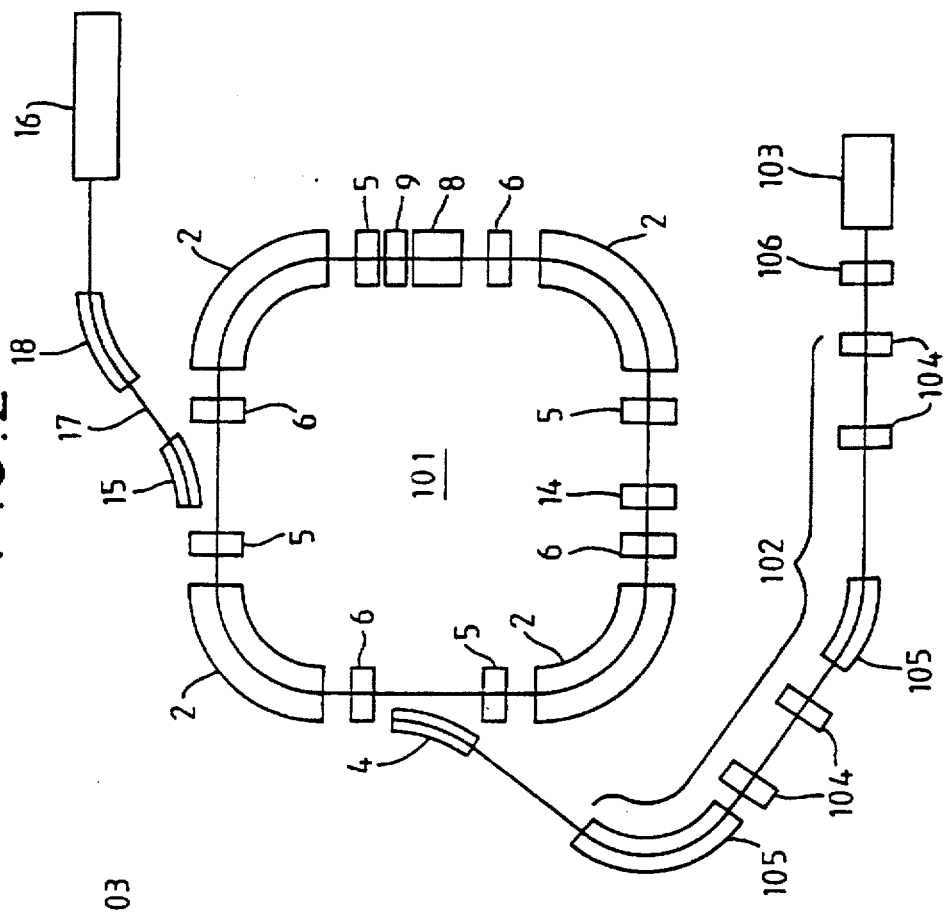
FIG. 1 is a schematic view showing a first example of a medical device according to the present invention.
Figure 2:
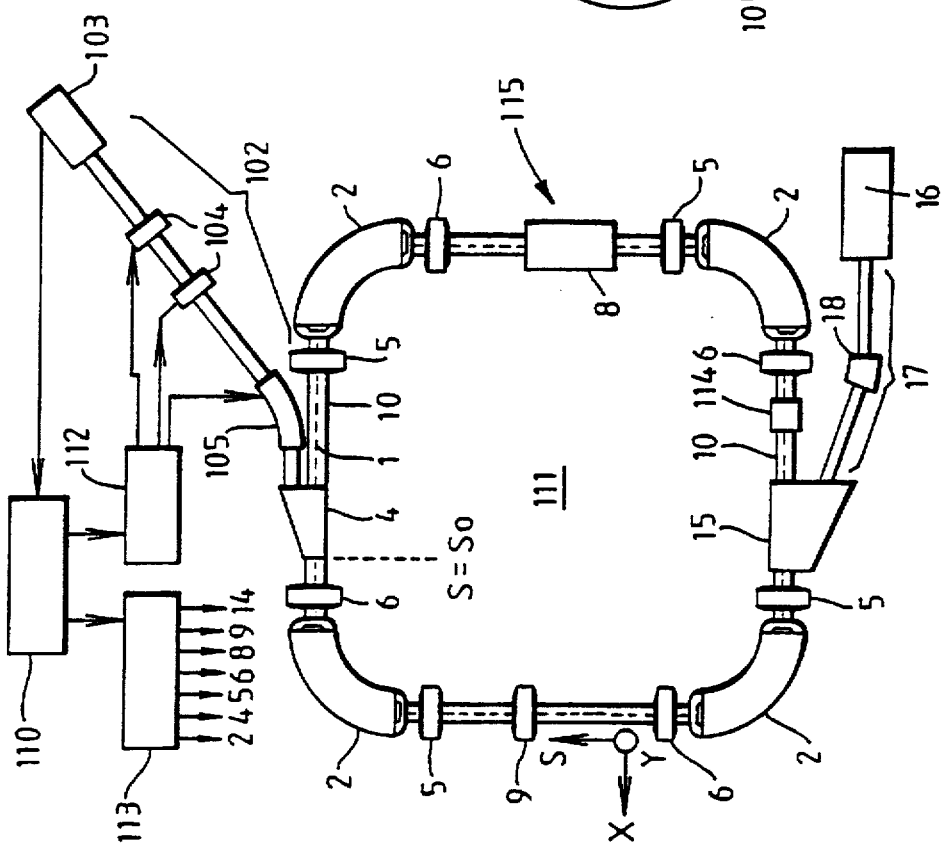
FIG. 2 is a schematic view of a prior art medical device.
Figure 3:
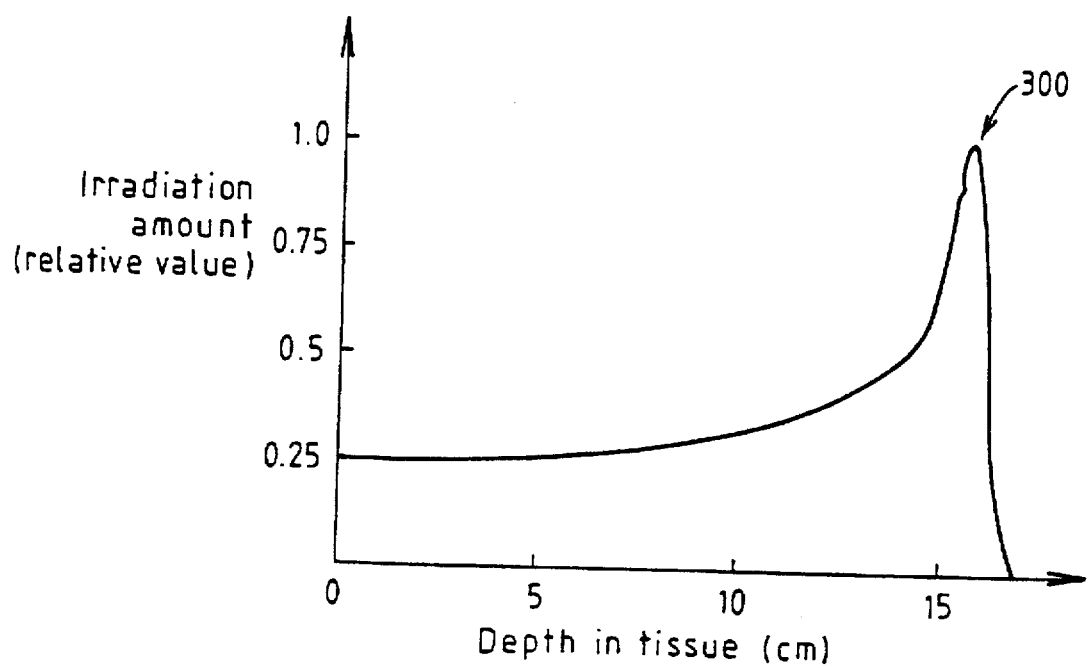
FIG. 3 is a graph of irradiation level/depth of penetration, showing Bragg's peak, for an ion beam.
Figure 4:
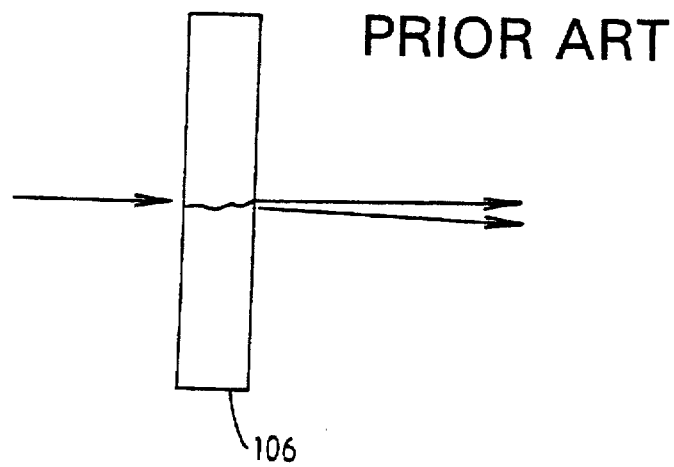
FIG. 4 is a diagrammatic view showing an example of a range controller.
Figure 5A:
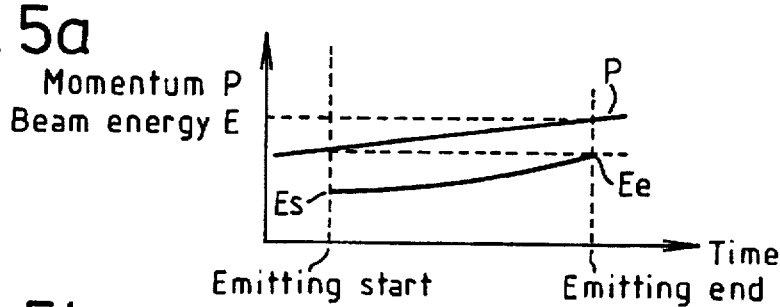
FIGS. 5a–5f are a number of graphs showing a method of operation of the device of FIG. 1.
Figure 5B:
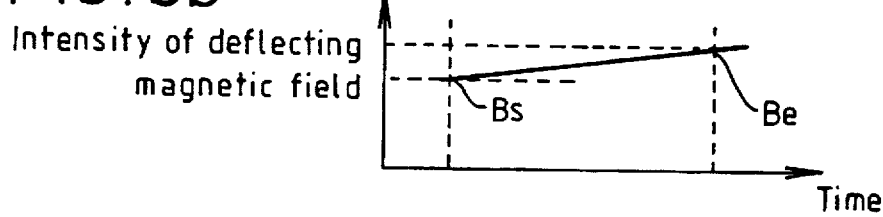
Figure 5C:
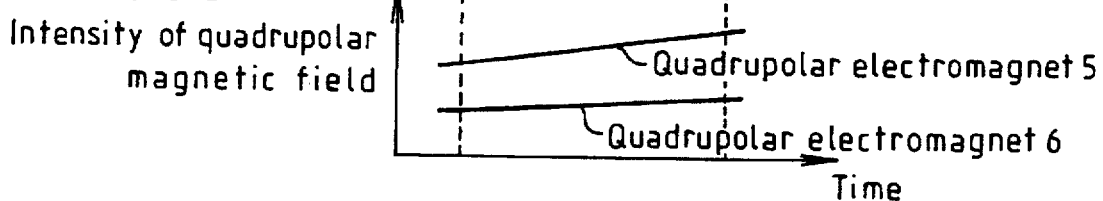
Figure 5D:
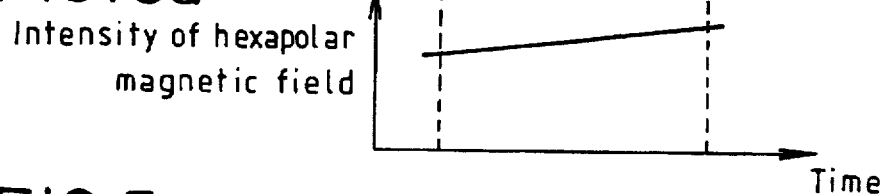
Figure 5E:
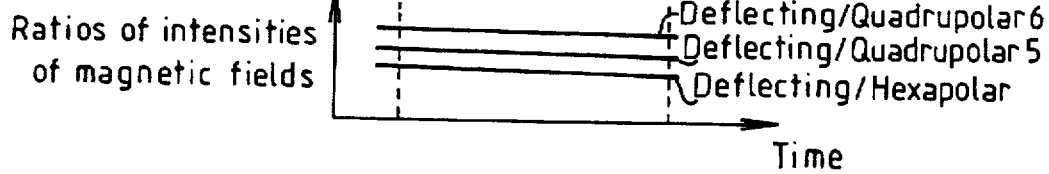
Figure 5F:
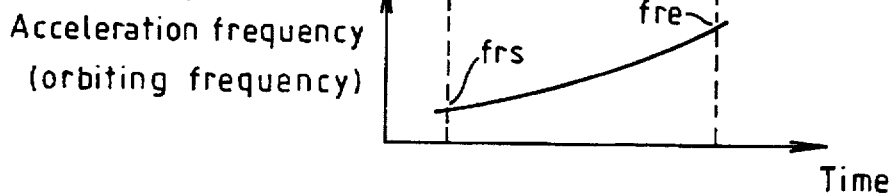

FIG. 1 shows a first example in which the present invention is applied to a medical device. In this example, protons having an energy of approximately 20 MeV are accelerated to an energy of between 50 and 300 MeV by an accelerator, and the proton beam is used for irradiation treatment.

This medical device includes a prestige accelerator 16 which generates a proton beam, prestige-accelerates and emits it. An injecting beam transporting system 17 then transports the beam which has been extracted from the prestige accelerator 16 to an accelerator 111 and injects it in the accelerator.

The accelerator accelerates the beam in a circulation chamber, generally illustrated 115, accumulates and emits it. An extracting beam transporting system 102 transports the beam which has been extracted from the accelerator 111 to a medical treatment chamber 103, the medical treatment chamber 103 being for performing an irradiation medical treatment using the beam. There is also a control device 110 for controlling various constituting instruments.

The accelerator 111 includes an injector 15 for injecting the beam, a radio frequency accelerating cavity 8 for providing an energy to the beam, bending electromagnets 2 for bending the orbital path of the beam, quadrupole electromagnets 5 for converging and correcting the orbital path of the beam, quadrupole electromagnets 6 for diverging the beam, a hexapole electromagnet 9 for exciting the resonance in the beam, a radio frequency applying device 114, such as an electrode, for increasing an amplitude of the betatron oscillation of the beam within the stability limit of the resonance, and an extractor 4 for extracting the beam. A multipole electromagnet other than a hexapole electromagnet, such as an octapolar electromagnet, can be used as the electromagnet for exciting the resonance.

The injecting beam transporting means 17 is provided with a bending electromagnet 18. The extracting beam transporting system 102 is provided with quadrupole electromagnets 104 and a bending electromagnet 105.

Among these instruments, the hexapole electromagnet 9, the radio frequency applying device 114, the extractor 4, the quadrupole electromagnets 104 and the bending electromagnet 105 are used only in the procedure of extracting the beam.

In operation, in the medical treatment chamber 103 the operator determines a beam energy Es which the beam is desired to have at the start of the extracting, and a beam energy Ee which is required at the end of the extracting. Es and Ee may be in a range of 50 through 300 MeV and may be based on affected part information (depth or size of affected part) of a patient and the like. The operator transmits signals corresponding these requirements to the control device 110. The control device 110 controls a power source 112 for instruments of the extracting beam transporting system and a power source 113 for instruments of accelerator (2,4,5,6,8,9,114, as shown).

Figure 13A:
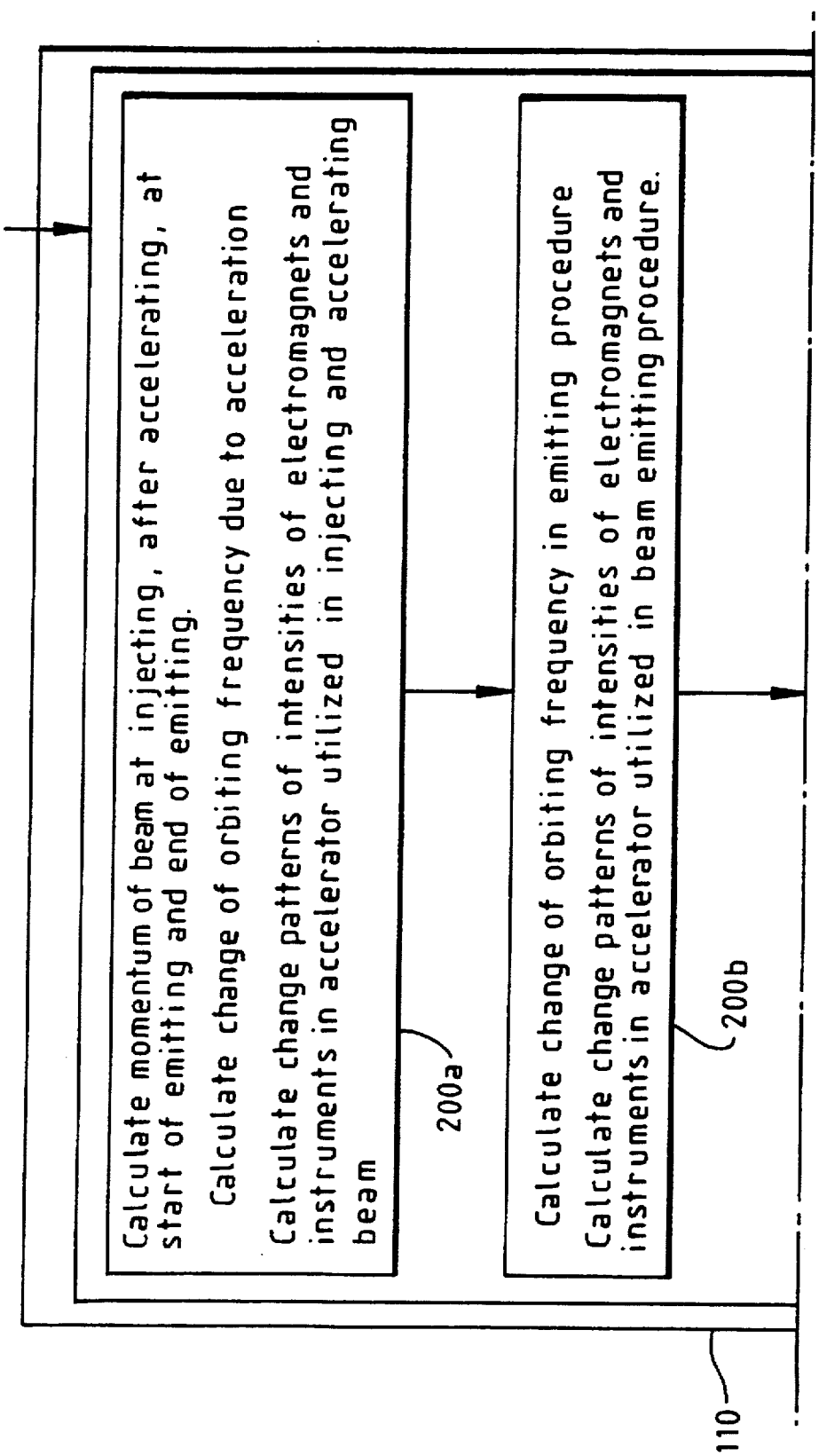
FIGS. 13A and 13B are a detailed flow chart for a control device for the devices of FIG. 1 and FIG. 10.
Figure 13B:
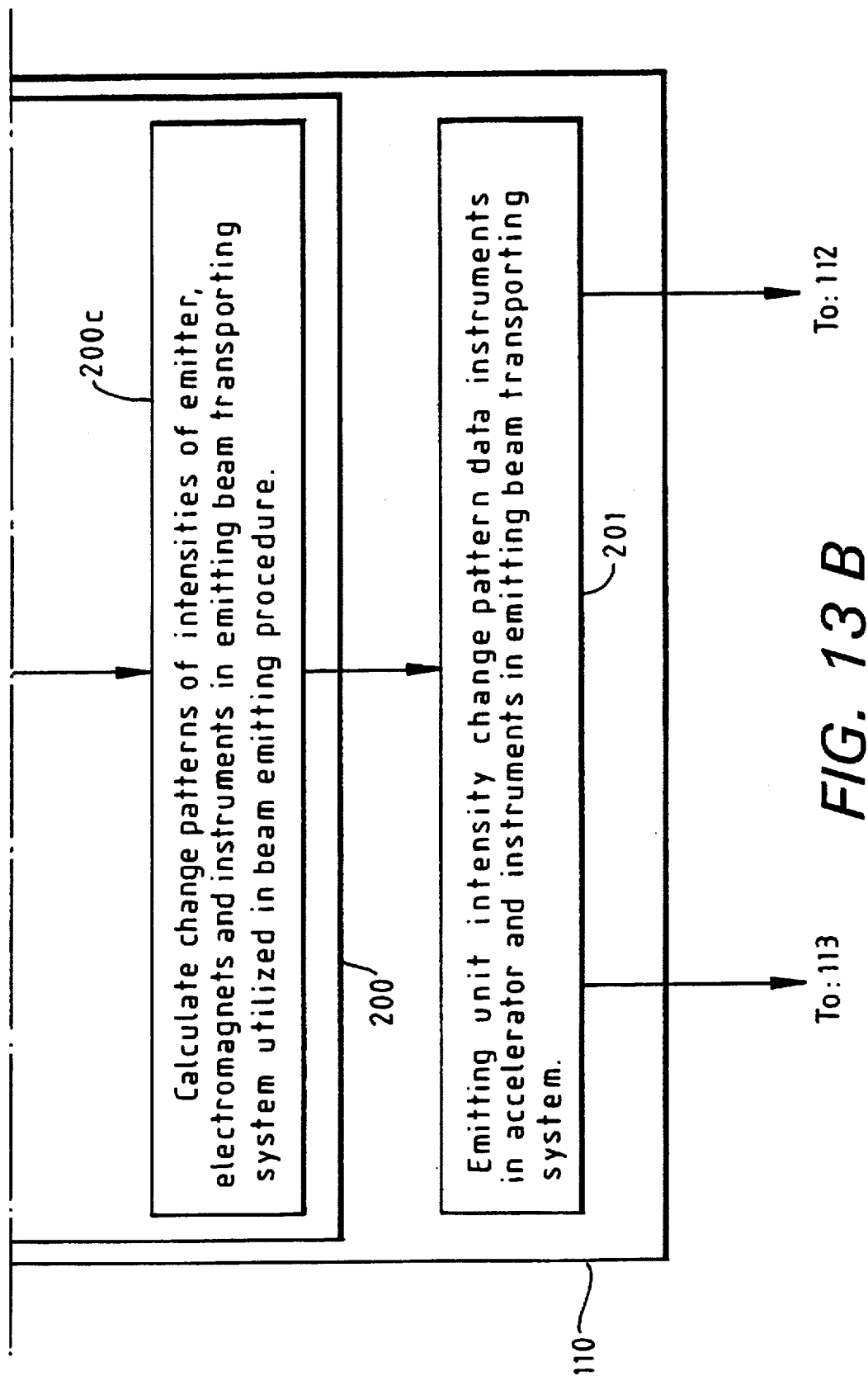

As shown by FIG. 13, the control device 110 includes a calculating unit 200 into which information from the medical treatment chamber is input (such as extracting start energy Es and extracting end energy, Ee), and which is used for calculating change patterns of intensities of instruments, and a pattern data transmitting unit 201 for transmitting control signals of the intensities of the instruments to the power sources 112 and 113 based on the calculation result.

The content of the pattern calculation in the calculation unit 200 is classified into 200a, 200b and 200c.

In 200a, first, the operation calculates momentums Pi and Ps of the beam corresponding to an energy Ey of the injecting beam and an extracting start energy Es therefrom, based on which the operation calculates change patterns of the intensities of instruments which are employed in the acceleration from the injection of the beam up to the energy Ee. In this way, as shown in FIG. 5, the intensities of the instruments can linearly be changed by linearly increasing the momentum, and therefore, the pattern setting and the control of the intensities of instruments are facilitated.

The orbital path of the beam 1 (shown schematically by a dashed line in FIG. 1) which has been injected from the injector 15 is bent in the orbiting procedure by the bending electromagnets 2, and is corrected by changing the gradient of the orbital path by the quadrupole electromagnets through a force which is proportional to a deviation from a designed orbital path (normally an orbital path in which centers of the vacuum ducts 10 are connected).

The quadrupole electromagnets 5 are used to change the gradient of the orbital path in a direction for converging the beam in the horizontal direction, whereas the quadrupole electromagnets 6 are used to change the gradient of the orbital path in a direction for diverging the beam in the horizontal direction. With respect to the vertical direction, the quadrupole electromagnets 5 are used to diverge the beam, whereas the quadrupole electromagnets 6 are used to converge the beam. The beam orbits while undergoing the betatron oscillation around the designed orbital path 1, and the frequency of the betatron oscillation can be controlled by excitation amounts of the quadrupole electromagnets 5 and 6.

In order to stably orbit the beam in the accelerator 11, in the procedures of injecting and accelerating it is desirable to render the betatron frequency (tune) per one turn of the accelerator with a value which will not cause resonance. In this example, the quadrupole electromagnets 5 and 6 are controlled such that the tune vx in the horizontal direction is 2.25 and tune vy in the vertical direction is 1.25. At this occasion, the intensities of the magnetic fields of the bending electromagnets 2 and the quadrupole electromagnets 5 and 6 are calculated based on the momentum Pi in injecting the beam. Under this state, the beam stably orbits in the accelerator and is provided with energy from the radio frequency accelerating cavity 8.

The frequency f of a radio frequency signal which is applied on the radio frequency accelerating cavity 8 is given a frequency fri for orbiting the beam, energy is provided to the beam from the radio frequency accelerating cavity 8, and, while maintaining constant respective ratios of intensities of magnetic fields of the bending electromagnets 2 versus the quadrupole electromagnets 5, and the bending electromagnets 2 versus the quadrupole electromagnets 6, the intensities of the magnetic fields are increased.

The orbiting frequency fri is calculated by the peripheral length of the accelerator 111 and the momentum of the beam. Thereby, the radius of curvature of the orbital path of the beam is decreased at curved portions of the bending electromagnets 2 and an orbital path of one turn is shortened. As a result, the beam is provided with a radio frequency energy from the radio frequency accelerating cavity 8 and the beam energy is increased. Further, an increase in the centrifugal force by the increase in the beam energy and an increase in the centripetal force by the increase in an excitation amount of the bending electromagnets 2 are balanced and the beam orbits centering on the same orbital path.

When the beam energy increases, the frequency whereby the beam orbits the accelerator increases. Therefore, the frequency of the radio frequency signal which is applied on the radio frequency accelerating cavity 8 is increased to match the orbiting frequency of the beam. In this procedure, the necessary intensities of the magnetic fields of the bending magnets 2 and the quadrupole electromagnets 5 and 6, and the voltage and the frequency of the radio frequency of the radio frequency accelerating cavity 8 are calculated in step 200a of FIG. 13.

In this accelerating procedure, the tune is maintained constant since the respective ratios of intensities of the magnetic fields of the bending electromagnets 2 versus the quadrupole electromagnets 5, and the bending electromagnets 2 versus the quadrupole electromagnets 6, are maintained constant.

Figure 6:
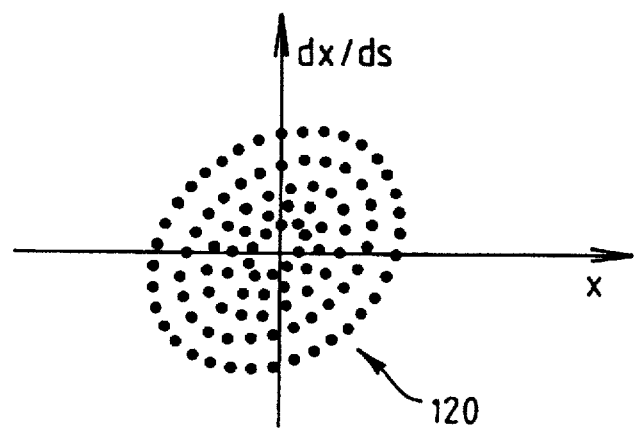
FIG. 6 is a graph showing a phase space of a beam, prior to emission, for the device of FIG. 1.

FIG. 6 shows the loci of the charged particles on the phase space (x, dx/ds) at the injection position s=s0 in the s direction (the direction of designed orbital path) in the accelerating procedure. With respect to the loci in the phase space of the view, there are a number of similar ellipses 120 having different diameters. The size of the diameter of the ellipse corresponds to the size of the amplitude of the betatron oscillation of the beam, and the smaller the diameter of the ellipse, the smaller the amplitude of the betatron oscillation.

After calculating intensity patterns of the instruments which are employed in the acceleration up to the energy Es in step 200a of FIG. 13, the operation calculates, in step 200b, the intensity patterns of instruments in the accelerator 111 when the beam is extracted while changing the beam energy. In step 200c, the operation calculates change patterns of intensities of the extractor 4 and the instruments of the extracting beam transporting system 102 which are employed for transporting the beam which has been extracted to the medical treatment chamber 103. The change pattern data of the intensities of the instruments, which have been calculated at the calculating unit 200 of FIG. 13, are transmitted to the power sources 112 and 113 from a transmitting unit 201, and control the respective power sources based on these pattern data.

Next, an explanation will be given of a method of operation in the extracting procedure by using a flow chart shown in FIG. 7. The operational method is performed in the following steps of (1) through (8).

(1) The control device controls the power source for the quadrupole electromagnets 5 for converging and the quadrupole electromagnets 6 for diverging, and sets the tune in the horizontal direction as vx=2.30.

The ratio of intensities of the magnetic fields of the quadrupole electromagnets 5 for converging versus the bending electromagnets 2 at this moment is defined as R1, whereas the ratio of intensities of the magnetic fields of the quadrupole electromagnets 6 for diverging versus the bending electromagnets 2, is defined as R2.

(2) The control device initiates an exciting current for exciting the resonance in the hexapole electromagnets 9.

The current flowing in the hexapole electromagnets 9 has a value such that particles having a large amplitude of the betatron oscillation among the orbiting beam are contained in the stability limit of the resonance. This value is provided by a previous calculation or by repetitive extracting operations.

Figure 8:
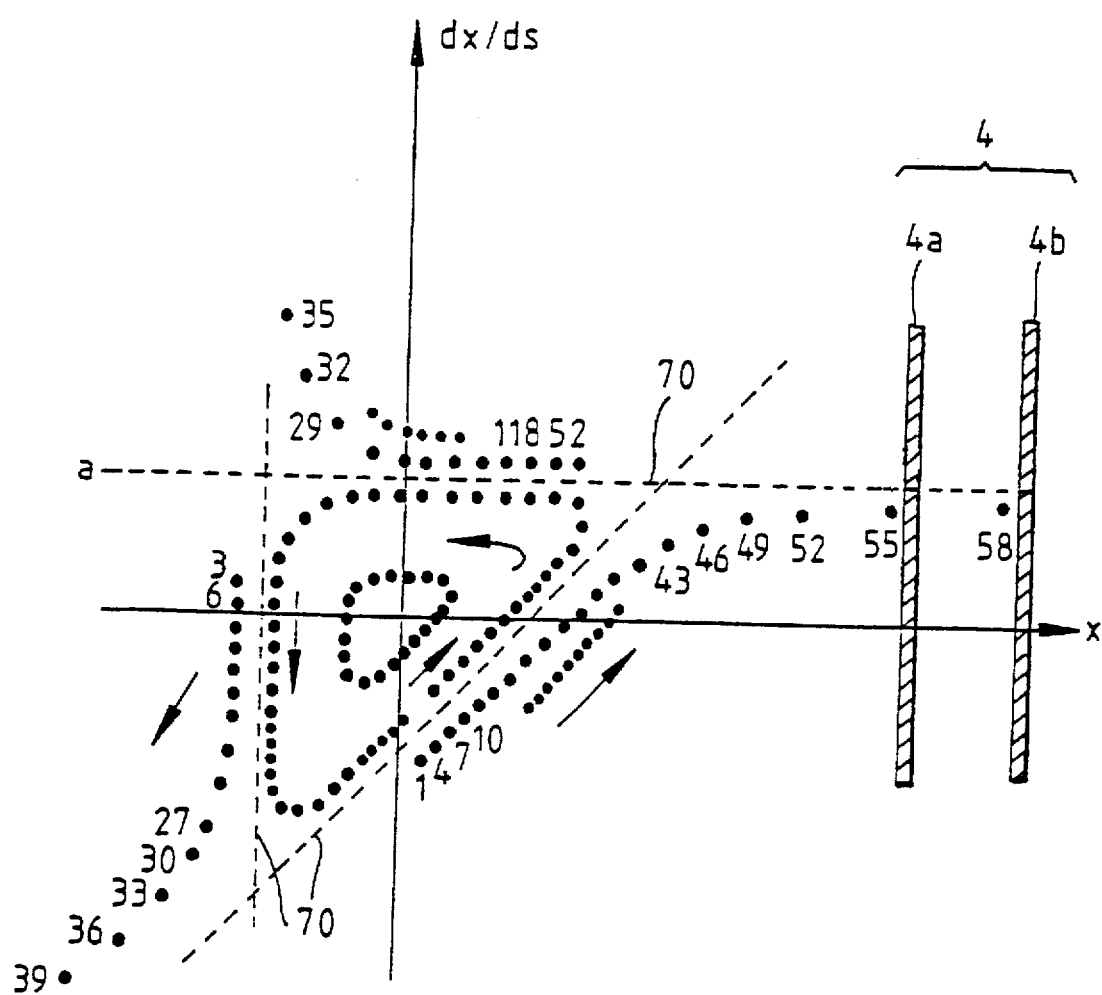
FIG. 8 is a graph showing a phase space of a beam at emission, for the device of FIG. 1.

A ratio of intensities of the magnetic fields of the bending electromagnets 2 versus the hexapole electromagnet 9 is defined as R3. At this moment, as shown in FIG. 8, the loci of the charged particles on the phase space at a position of the injector 4 have a triangular shape.

(3) A radio frequency electromagnet field having a wide frequency band which is irregularly time-varying is applied by the radio frequency applying device 114 to the beam.

Figure 9A:
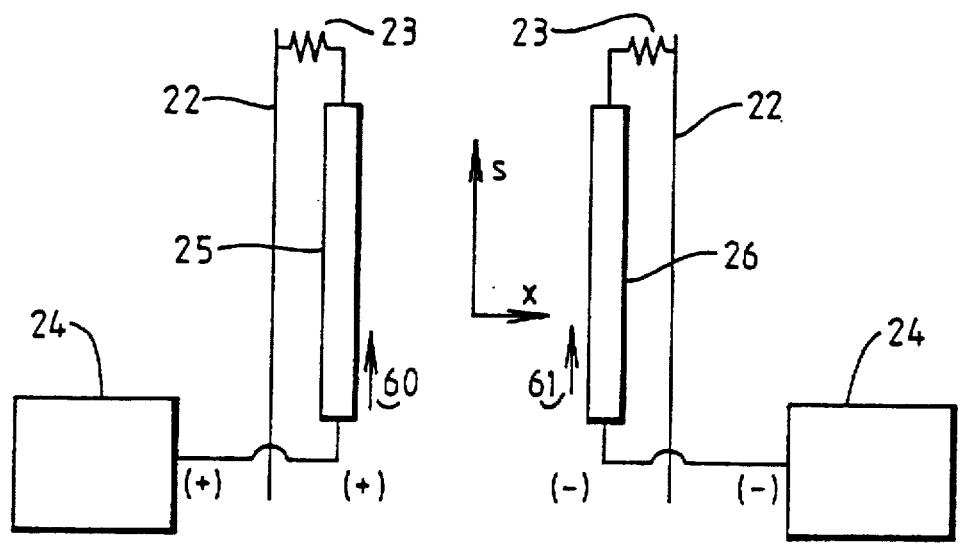
FIG. 9a is an explanatory view of a radio frequency applying device, for use in the device of FIG. 1.
Figure 9B:
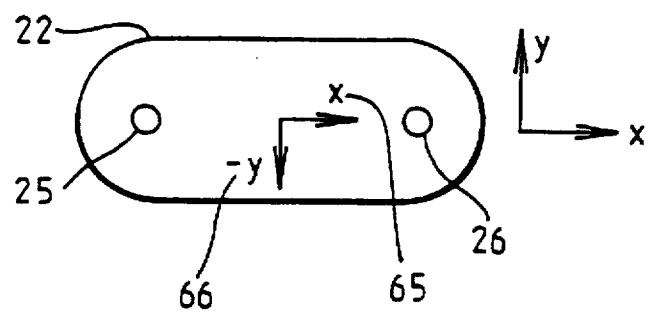

FIGS. 9a and 9b show the construction of the radio frequency applying device 114. The electrodes 25 and 26 in this view are rod-like electrodes in a vacuum duct 22 opposing each other in the horizontal direction (x direction in the diagram, which is perpendicular to the circulating beam progressing direction s), to each of which is applied a time-varying signal. By passing opposite currents (60, 61) from a wide band radio frequency power source 24 through the rod-like electrodes, an electric field 65 in the x direction and a magnetic field 66 in −y direction are applied on the beam as shown in FIG. 9. Load resistors 23 are installed such that the applied currents do not reflect to the side of the radio frequency power source 24 from end portions of the electrodes.

The radio frequency current supplied from the radio frequency power source 24 is an irregular signal, and is provided with a frequency spectrum including a frequency band of approximately 0.25 frs through 0.35 frs where frs is an orbiting frequency when the energy of the beam is Es. That is, the signal is provided with the frequency spectrum having a central frequency of 0.30 frs and the frequency width Δf of 0.1 frs.

The reason for providing such a frequency component is that the tune of the beam varies depending upon the amplitude of the betatron oscillation. That is, the tune of the beam having an extremely small amplitude of betatron oscillation is 2.30, which is set by the quadrupole electromagnets. However, the tune of the beam having a large amplitude of betatron oscillation which is near to the stability limit, is deviated from this value by 2.3333−2.30=0.0333, approximately by the influence of the hexapole electromagnet 9 for generating the resonance.

Accordingly, since the tune of the beam of which amplitude of oscillation is in the above range is continuously distributed between 2.3333 through 2.30, it is desirable to provide the frequency components including the tune distribution of the beam for increasing the amplitude of the betatron oscillation of all the beams in the stability limit.

In this way, by applying the radio frequency electromagnetic fields on the beam from the radio frequency applying device 114, the gradient of the orbital path of the beam varies by the operation of the electric field and the magnetic field, the amplitude of the betatron oscillation of the beam in the phase space shown by FIG. 8 increases, and the amplitude of the betatron oscillation of particles exceeding the stability limit (designated by lines 70), rapidly increases by the resonance. Numerals shown in the phase space of FIG. 8 designate numbers of orbits, and the particles enter between the electrodes 4a and 4b of the extractor by the orbiting and are extracted from the extractor 4.

(4) The control device changes the intensities of the magnetic fields of the bending electromagnets 2 from Bs to Be.

(5) Simultaneously with (4) the control device changes the frequency of the radio frequency electromagnetic field which is applied on the beam from the radio frequency accelerating cavity 8, from frs to fre.

(6) Simultaneously with (4) the control device changes the intensities of the magnetic fields of the quadrupole electromagnets 5 and 6, and the hexapole electromagnet 9 such that the ratios of the intensities of the magnetic fields R1, R2 and R3 remain constant.

In the procedure the orbiting frequency changes from frs to fre since the energy of the orbiting beam changes from Es to Ee. FIGS. 5a–5f shows changes over time of the energy (FIG. 5a), the momentum (FIG. 5a), and the orbiting frequency of the beam (FIG. 5f), and the intensities of the respective magnetic fields (FIGS. 5b–5e) in the extracting procedures of (4) through (6).

(7) Simultaneously with (4), the control device changes the central frequency of the radio frequency electromagnetic field which is applied to the beam from the radio frequency applying device 14 from 0.3 frs to 0.3 fre while maintaining the frequency width as âof=0.1 frs.

With the change of the orbiting frequency of the beam from frs to fre, the frequency in synchronism with the betatron oscillation also changes. Therefore, it is possible to increase the amplitude of the betatron oscillation of the respective particles by changing the energy of the beam by the procedure (7). Accordingly, particles having a small initial amplitude of the betatron oscillation finally exceed the stability limit (shown in FIG. 8), and are extracted from the extractor 4. In the phase space of FIG. 8, the stability limit remains constant, and the gradient of orbital path dx/ds at the entrance of the extractor 4 remains constant during the extracting procedure.

The control of the above steps (4) through (7) is previously calculated at the calculating unit 200b of the control device 110 such that the momentum of the beam performs a desired change, and is carried out by transmitting the pattern signals from the transmitting unit 201 to the power source 113 for the instruments of the accelerator. In this way, it is possible to extract the beam while changing the energy thereof.

(8) Simultaneously with (4), the control device changes the intensities of the extractor 4 and the constituent instruments of the extracting beam transporting system 102 in correspondence with the change in the energy of the beam.

That is, the operation changes the intensities such that ratios among the intensity of the injector 4, the intensities of the magnetic fields of the bending magnets 105 and the quadrupole electromagnet 104 of the extracting beam transporting system 102, and the intensity of the magnetic fields of the bending electromagnets 2 of the accelerator 111, are maintained constant.

The control device previously calculates the change of the intensities of the injector 4 and the constituent instruments of the extracting beam transporting system 102 using the calculating unit 200c of the control device 110, transmits the pattern signals from the transmitting unit 201 to a power source for the extractor 4 in the power sources 113 and 112 and controls them in synchronism with the other instruments of the accelerator.

As is shown in FIG. 8, since the beam is extracted while maintaining the stability limit although the energy of the beam is changing, the gradient of orbital path at the entry portion of the extractor 4 is made constant. Further, a beam having a small diameter can continuously be extracted to the medical treatment chamber 103 by maintaining constant the ratios of the intensities among the extractor 4, the constituent instruments of the extracting beam transporting system 102 and the bending electromagnets 102.

Figure 10:
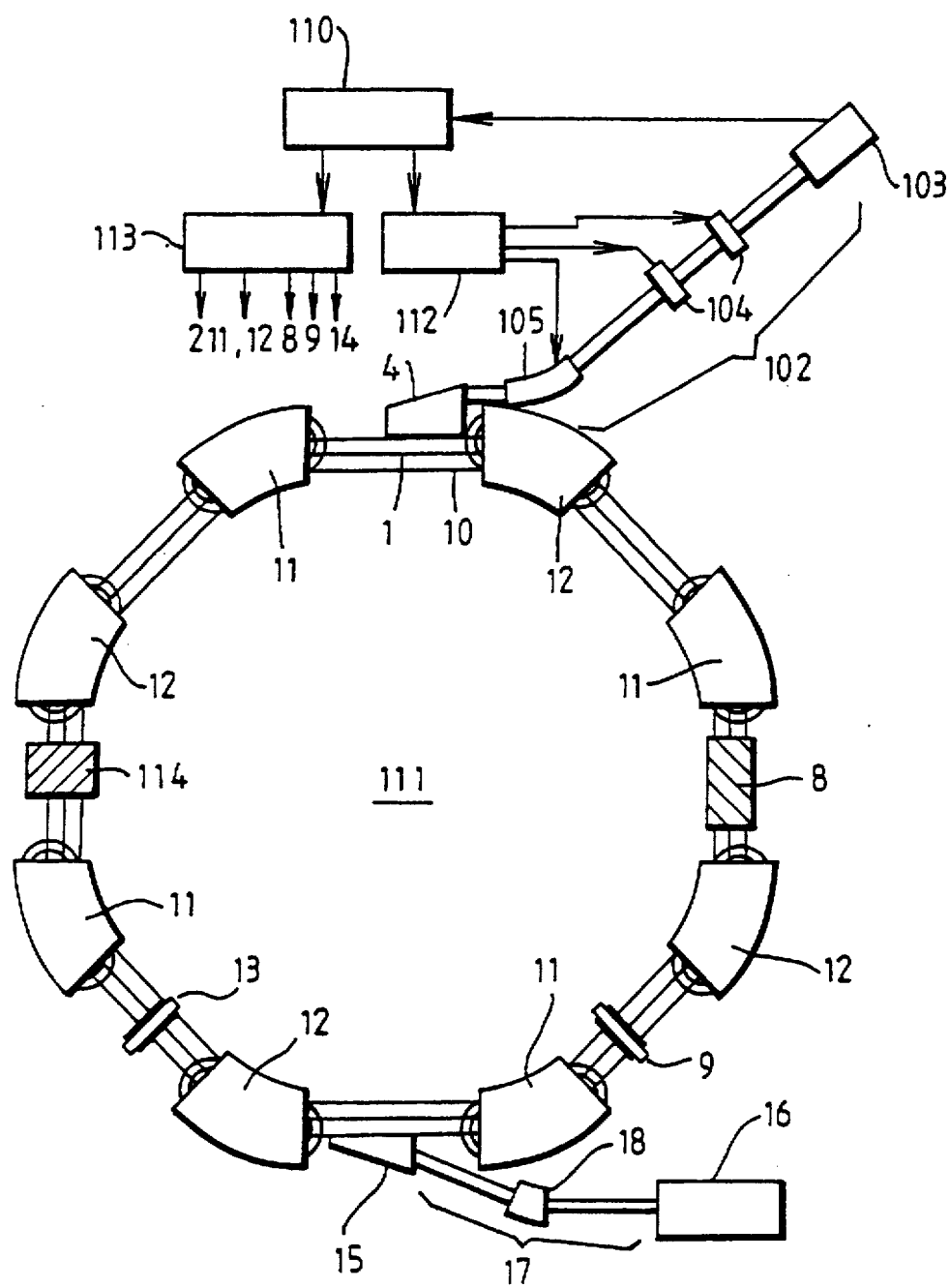
FIG. 10 is a schematic view showing a second example of a medial device according to the present invention.

Next, an explanation will be given of a second example of the present invention shown in FIG. 10, wherein the present invention is applied to a medical device. This example is different from the first example of FIG. 1, and a bending electromagnet 11 is provided with a function of the quadrupole electromagnet for converging, a bending electromagnet 12 is provided with a function of the quadrupole electromagnet for diverging, and a number of the quadrupole electromagnets used in the first example are omitted. Only a quadrupole electromagnet 13 is utilized for adjusting the tune, the other constituting instruments are the same as in the first example (and the same reference numbers are used), and the explanation thereof will be omitted.

The bending electromagnet 11 is provided with a function of bending the orbital path of the beam along with converging the beam in the horizontal direction, whereas the bending electromagnet 12 is provided with a function of bending the orbital path of the beam along with diverging the beam in the horizontal direction.

Figure 11:
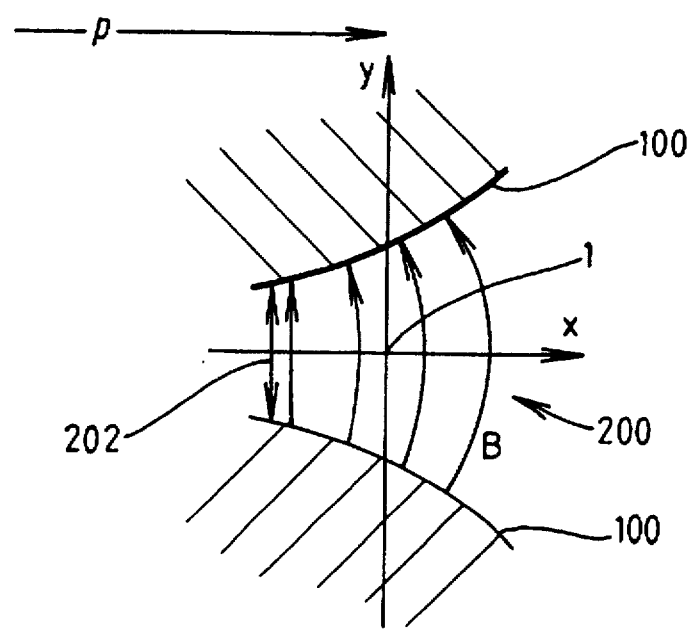
FIG. 11 is a graph for the area around a magnetic pole of a bending electromagnet of the device of FIG. 10.

Next, an explanation will be given of the quadrupole electromagnetic fields which are generated by the bending electromagnets 11 and 12. FIG. 11 shows a detailed diagram around a magnetic pole of the bending electromagnet 12. Numeral 100 designates an magnetic pole surface facing a gap 200, the center of the radius of curvature of the electromagnet is on the side of the negative direction of x axis, the gap interval 202 is enlarged toward the outer side (the side of the positive direction of x axis) in the diameter direction.

By this construction of the magnetic electrode, the intensity of the magnetic field B in the vertical direction (y direction) decreases toward the outside in the diameter direction, the intensity of the magnetic field in the horizontal direction, or x direction, increases toward a direction leaving from the plane of y=0, and therefore, a quadrupole magnetic field component is generated.

When the gap interval 202 is set such that the intensity of the magnetic field By in the vertical direction satisfies the relationship of the following equation, the gradient of the orbital path of the beam changes by a force which is in proportion to (1−n) in the horizontal direction, and to n in the vertical direction.

$$By = B_o(r/\rho)^{-n} \ldots \quad \text{(Equation 1)}$$

where $B_o$ is a constant, $\rho$ is a radius of curvature of the designed orbital path, r is a distance from the center of the radius of curvature, and n is a real number. The tune of the beam can be set to a desired value by suitably selecting the size and the sign of n in equation 1.

The bending electromagnet 11 is provided with the function of bending the beam as well as the function of converging the beam in the horizontal direction by rendering n to be negative, whereas the bending electromagnet 12 is provided with a function of bending the beam as well as the function of diverging the beam in the horizontal direction by rendering n to be more than 1. By suitably selecting the value of n for the bending electromagnets 11 and 12, the tune in the horizontal direction is made 2.25 and the tune in the vertical direction is made 1.25.

As in the first example, the beam injected into the accelerator 111 is firstly accelerated up to the energy of Es so that the energy range of the extracting beam is rendered from Es to Ee by the information of the medical treatment chamber 103. However, acceleration up to the energy Es is carried out by increasing the intensities of the magnetic fields of the bending electromagnets 11 and 12 and by increasing the frequency of the radio frequency electromagnetic field which is applied to the beam from the radio frequency accelerating cavity 8.

In this procedure, the intensities of the magnetic fields of the bending electromagnets 11 and 12 along with the frequency of the radio frequency electromagnetic field of the radio frequency accelerating cavity 8, are previously calculated at the calculating unit 200a of the control device 110, and are controlled by transmitting pattern data from the transmitting unit 201 to the power source 113.

Further, in the acceleration up to the energy Es the quadrupole electromagnet 13 is not utilized. In this way, the energy can be increased up to Es as in the first example by increasing the intensities of the magnetic fields of the bending electromagnets 11 and 12, and the frequency of the radio frequency electromagnetic field which is applied to the beam from the radio frequency accelerating cavity 8.

Figure 12A:
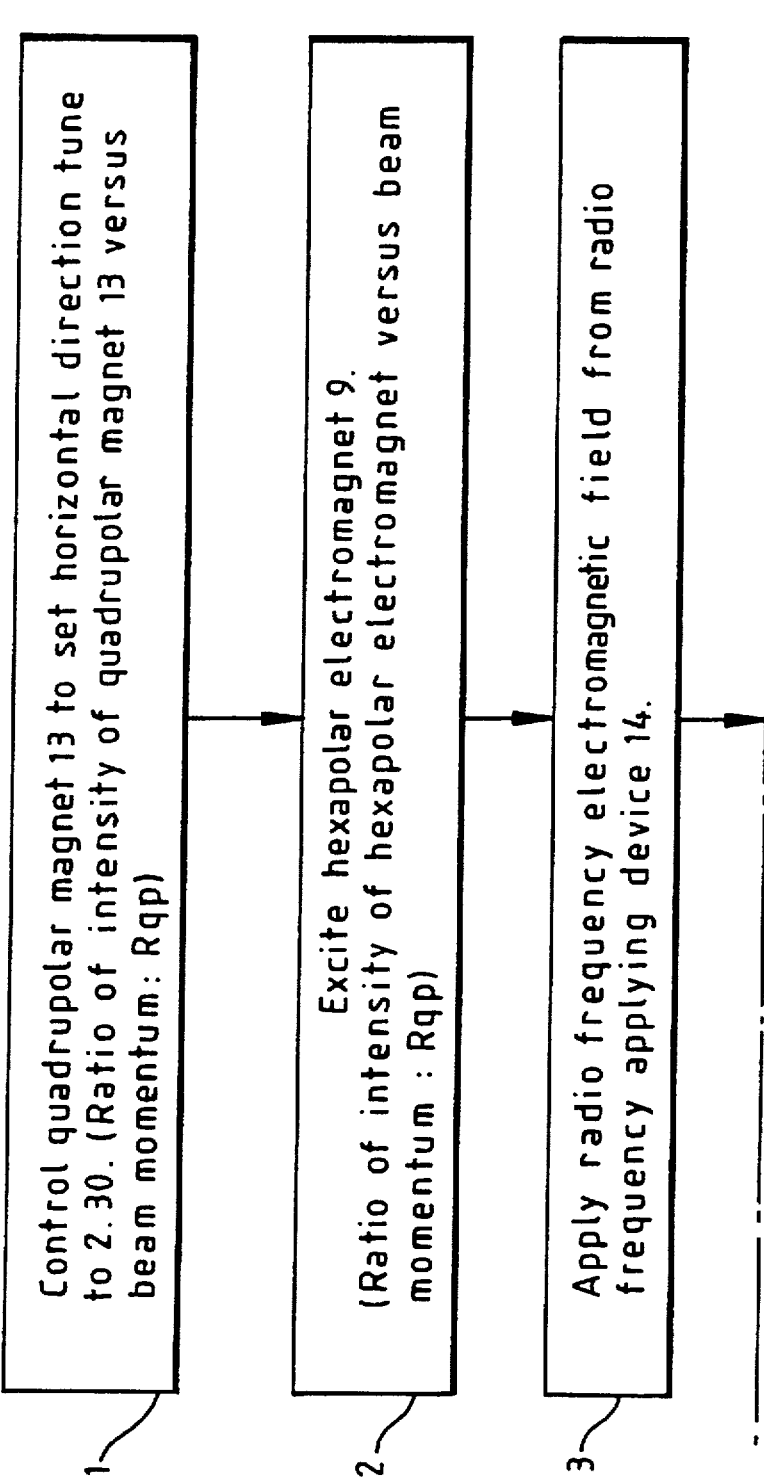

Next, an explanation will be given of a method of operation of an extracting procedure for the second example, as shown in FIG. 12.

The method of operation includes the steps (1) through (6).

(1) The operation sets the tune in the horizontal direction to 2.30 by the quadrupole electromagnet 13 before starting the extracting.

A ratio of the intensity of the magnetic field of the quadrupole electromagnet 13 versus the momentum of the beam is defined as Rqp. In the first example, the ratio of the intensities of the magnetic fields of the quadrupole electromagnets versus the bending electromagnets has been considered. By contrast, in this example, the ratio of the momentum of the beam versus the intensity of the magnetic field of the quadrupole electromagnet is considered since, in this example, the momentum of the beam is made to change while maintaining the intensity of the magnetic fields of the bending electromagnets.

(2) The current for exciting a resonance in the hexapole electromagnet 9 is initiated.

The operation provides the current flowing in the hexapole electromagnet 9 with a value to a degree whereby particles having large amplitudes of the betatron oscillation in the orbiting beam are contained in the stability limit, which is obtained by a previous calculation or through repetitive extracting operations. A ratio of the intensity of the magnetic field of the hexapole electromagnet 9 versus the momentum of the beam is defined as Rsp.

(3) The operation applies a radio frequency electromagnetic field having a wide band which is irregularly time-varying from the radio frequency applying device 114 to the beam.

The radio frequency which is applied from the power source 24 to the radio frequency applying device 114 is rendered an irregular signal, and a frequency spectrum including a range of a varying frequency of the betatron oscillation, that is a band of approximately 0.25 frs to 0.35 fre, is provided to simply achieve the increase of the amplitude of the betatron oscillation in the procedure of changing the beam energy from Es to Ee. At this stage, frs and fre are the orbiting frequencies when the beam energies are Es and Ee.

By providing these frequency components, all the frequency components of the betatron oscillation in the energy range from the start to the end of extracting, are included, and therefore it is not necessary to change the frequency spectrum as stated in the first example. By applying the radio frequency electromagnetic field to the beam from the radio frequency applying device 114, the amplitude of the betatron oscillation of the beam increases by changing the gradient of the orbital path of the beam by the operation of the electric field and the magnetic field, and the amplitude of the betatron oscillation of particles exceeding the stability limit shown in FIG. 8 rapidly increases by the resonance and the particles are extracted from the extractor 4.

(4) The operation changes the frequency of the radio frequency electromagnetic field which is applied to the beam from the radio frequency accelerating cavity 8 from frs to fre while maintaining constant the intensities of the magnetic fields of the bending electromagnets 11 and 12.

At this stage frs and fre designate the orbiting frequencies of the beam when the energies are Es and Ee.

(5) Simultaneously with (4), the operation changes the intensities of the magnetic fields of the quadrupole electromagnets 13 and the hexapole electromagnet 9 so that Rqp and Rsp remain constant.

The change of the intensities of the magnetic fields in (4) and (5) are controlled by transmitting as pattern signals the change patterns of the intensities of the instruments, which have been obtained at the calculating unit 200b of the control device 110, from the transmitting unit 201 to the power source 113 for the instruments of the accelerator.

(6) Simultaneously with (4), the operation changes the intensities of respective instruments, such that the ratios of the momentum of the beam versus the intensities of the instruments of the extractor 4 and the constituent instruments of the extracting beam transporting system 102, remain constant.

That is, the operation changes the intensities of the injector 4, and the bending electromagnet 105 and the quadrupole electromagnets 104 of the extracting beam transporting system 102 so that the ratios of the momentum of the beam and the intensities of the respective instruments remain constant. In this way, the gradient of the orbital path at the entry portion of the extractor 4 remains constant although the beam energy is changing, and therefore a beam having a small diameter can continuously be extracted to the medical treatment chamber 103.

The change of the intensities of the instruments of (6) is controlled by transmitting as pattern signals the change patterns of the intensities of the instruments, which have been calculated at the calculation unit 200c of the control device 110, from the transmitting unit 201 to the power source 113 for the instruments of the accelerator.

Further, in the above examples, an explanation has been given to the example wherein the beam is extracted while changing the beam energy of proton in a range of 50 through 300 MeV. However, it is possible to extract the beam while varying the beam energy in an energy range of approximately 50 to 800 MeV similarly (or any other suitable range), even if heavy ions such as C or Ar are employed.

While the invention has been illustrated by embodiments, it is not restricted to them. Modifications and variations are possible within the inventive concept.

What is claimed is:

1. Apparatus for acceleration of a charged particle beam, the apparatus having:

a circulation chamber, for circulation of a charged particle beam, bending magnets for generating bending magnetic fields for bending a circulating beam circulating in said circulation chamber, a multipole magnet for generating a multipole magnetic field for specifying a stability limit of resonance of said circulating beam, energy means for altering the energy of said circulating beam, extraction means for extracting output beams from the apparatus, and control means arranged for altering the energy of said circulating beam using said energy means in the extraction of said output beams so as to alter the energy of the output beam and for maintaining substantially constant a stability limit of a resonance of the betatron oscillation of said circulating beam by using bending and multipole magnets while the output beams are being extracted.

2. Apparatus according to claim 1 wherein said control means are arranged to be operable to extract said output beams sequentially using said extraction means so that said output beams are joined to form a continuous beam.

3. Apparatus according to claim 1 wherein said control means are arranged to be operable to alter the energy of said circulating beam using said energy means at the same time as extracting said output beams using said extraction means.

4. Apparatus according to claim 1 wherein said extraction means include means for increasing an amplitude of a betatron oscillation of said circulating beam to exceed said stability limit, and said control means are operable to increase said amplitude in the extraction of said output beams by said extraction means.

5. Apparatus according to claim 4 wherein said means for increasing an amplitude of a betatron oscillation include means for applying a first electromagnetic field to said circulating beam in a direction transverse to the progressing direction of said circulating beam, and said control means are arranged to be operable to adjust said first electromagnetic field in the extraction of said output beams by said extraction means.

6. Apparatus according to claim 5 wherein said control means are arranged to be operable to alter the frequency of at least one component of said first electromagnetic field according to the variance of the energy of said circulating beam while the output beam is being extracted.

7. Apparatus according to claim 1 wherein said energy means include means for applying an electromagnetic field to said circulating beam in a direction along the progressing direction of said circulating beam, said control means being arranged to be operable to maintain the values of bending and multipole magnetic fields produced by bending and multipole magnets respectively in a substantially constant ratio in the extraction of said output beams by said extraction means.

8. Apparatus according to claim 1 including transportation means for transporting said output beams extracted from the circulation chamber, and an electromagnet for controlling said output beams in the transportation means, said control means being arranged to alter the magnetic field produced by said electromagnet in accordance with the energy of said output beams.

9. A method of operating a circular accelerator for a charged particle beam, the method including the steps of
   (i) maintaining a circulating beam circulating in a circulation chamber of said circular accelerator,
   (ii) maintaining substantially constant a stability limit of a resonance of betatron oscillation of said circulating beam,
   (iii) changing the energy of said circulating beam during step (i), and
   (iv) extracting an output beam from said circulation chamber while the energy of said output beam is being altered, wherein steps (ii), (iii) and (iv) are carried out substantially simultaneously.

10. A method according to claim 9 wherein the energy of at least one of said output beams varies while said output beams are extracted from said circulation chamber.

11. A method according to claim 9 wherein said output beams are joined to form a continuous beam.

12. A method according to claim 11 wherein the energy of said continuous beam varies while said continuous beam is extracted from said circulation chamber.

13. A method according to claim 9 wherein said step of extracting output beams includes the step of increasing an amplitude of a betatron oscillation of said circulating beam to exceed said stability limit.

14. A method according to claim 13 wherein the circular accelerator includes bending and multipole magnets for producing bending and multipole magnetic fields respectively, and the values of said bending and multipole magnetic fields remain substantially constant ratio in the step of increasing said amplitude of the betatron oscillation.

15. A method according to claim 13 wherein said amplitude of the betatron oscillation is increased by applying a first electromagnetic field to the circulating beam in a direction transverse to the progressing direction of said circulating beam.

16. A method according to claim 15 wherein said first electromagnetic field includes a plurality of radio frequency components at different frequencies.

17. A method according to claim 15 wherein the frequency of at least one component of said first electromagnetic field is altered in the step of increasing said amplitude of the betatron oscillation.

18. A method according to claim 9 wherein said step of changing the energy of said circulating beam includes the steps of:
   applying an electromagnetic field to said circulating beam in a direction along the progressing direction of said circulating beam so as to alter the energy of the output beam while the output beam is extracted from said circulation chamber; and
   adjusting bending and multipole magnetic fields produced by bending and multipole magnets respectively, wherein the values of said bending and multipole magnetic fields are maintained in a substantially constant ratio while the output beam is being extracted.

19. A method of varying the energy of an output charged particle beam over a predetermined range in an extraction process in which said output charged particle beam is extracted, the method including the step of:
   substantially simultaneously adjusting the operation of the following elements of a circular charged particle beam acceleration apparatus:
      (i) accelerating means for altering the energy of a circulating beam circulating in the apparatus;
      (ii) extraction means for extracting said output charged particle beam from the apparatus;
      (iii) a bending magnet and a multipole magnet for controlling a path of said circulating beam and maintaining substantially constant a stability limit of a resonance of betatron oscillation of said circulating beam; and
      (iv) a transport magnet for controlling said output charged particle beam.

20. Apparatus for acceleration of a charged particle beam, the apparatus having:
   a circulation chamber for circulation of a charged particle beam,
   energy means for altering the energy of a circulating beam circulating in the apparatus,
   means for extracting output beams from the apparatus;
   means for increasing an amplitude of a betatron oscillation of said circulating beam to exceed the stability limit of a resonance of said circulating beam which include means for applying a first electromagnetic field to said circulating beam in a direction transverse to the progressing direction of said circulating beam in the extraction of said output beams by said extracting beams;
   wherein said energy means include means for applying a second electromagnetic field to said circulating beam in a direction along the progressing direction of said circulating beam in the extraction of said output beams so as to alter the energy of said output beams while the output beams are being extracted,
   and the apparatus further includes bending and multipole magnets for producing bending and multipole magnetic fields respectively to control the orbital path of the circulating beam, and a controller which is adapted to be operable to simultaneously control the energy of said circulating beam and said first electromagnetic field, whilst maintaining the values of said bending and multipole magnetic fields in a substantially constant ratio in the extraction of said output beams by said extraction means.

21. An accelerator having electromagnets for orbiting a charged particle beam, and an extractor for extracting the beam, the accelerator comprising:
   bending electromagnets for generating a bending magnetic field for bending said charged particle beam;
   a multipole electromagnet for generating a multipole magnetic field for specifying a stability limit of resonance of said charged particle beam;
   radio frequency applying means for increasing an amplitude of a betatron oscillation of said charged particle beam within said stability limit by applying a first electromagnetic field;
   accelerating means for providing an energy thereto by applying a second electromagnetic field so as to accelerate said charged particle beam; and
   a control device for controlling the intensities of said bending and multipole magnetic fields so as to maintain the values of said bending and multipole magnetic fields in a substantially constant ratio while the output beam is extracted, and for controlling a frequency of said first electromagnetic field and a frequency of said second electromagnetic field so as to achieve a required change in energy of said charged particle beam while the output beam is extracted.

22. The accelerator according to claim 21 wherein said control device controls a ratio of an intensity of the multipole magnetic field versus a momentum of the beam so as to maintain said ratio approximately constant.

23. An apparatus for acceleration of a charged particle beam, comprising:

a circulation chamber for circulation of a charged particle beam;

bending electromagnets for generating bending magnetic fields for bending said charged particle beam;

a multipole electromagnet for generating a multipole magnetic field for specifying a stability limit of resonance of said charged particle beam;

power sources for altering the energy of a circulating beam circulating in said circulation chamber;

an extractor for extracting output beams from the apparatus; and a control device connected to said power sources for altering the energy of said circulating beam using said power sources in the extraction of said output beams in order to alter an energy level of the output beams, and for controlling the intensities of said bending and multipole magnetic fields so as to maintain the values of said bending and multipole magnetic fields in a substantially constant ratio while the output beams are being extracted.

24. An accelerator having electromagnets for orbiting a charged particle beam, and an extractor for extracting the beam, the accelerator comprising:

a radio frequency accelerating cavity for accelerating said charged particle beam by providing an energy thereto;

bending electromagnets for generating magnetic fields for bending said charged particle beam;

a multipole electromagnet for generating a multipole magnetic field for specifying a stability limit of resonance of said charged particle beam;

a radio frequency applying device for increasing an amplitude of a betatron oscillation of said charged particle beam within said stability limit; and a control device for controlling the intensities of said bending and multipole magnetic fields so as to maintain substantially constant a stability limit of a resonance of the betatron oscillation of said circulating beam, and for controlling a frequency of a first electromagnetic field generated by said radio frequency applying means and a frequency of a second electromagnetic field generated by said accelerating means so as to achieve a required change in energy of said charged particle beam while the output beams are being extracted.

* * * * *